(12) United States Patent
Kandiraju et al.

(10) Patent No.: US 11,088,826 B2
(45) Date of Patent: Aug. 10, 2021

(54) MANAGING ASSETS WITH EXPIRATION ON A BLOCKCHAIN

(71) Applicant: International Business Machines Corporation, Armonk, NY (US)

(72) Inventors: Gokul Bhargava Kandiraju, Briancilff Manor, NY (US); Krishna C. Ratakonda, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 243 days.

(21) Appl. No.: 15/907,140

(22) Filed: Feb. 27, 2018

(65) Prior Publication Data

US 2019/0268140 A1    Aug. 29, 2019

(51) Int. Cl.
| H04L 9/06 | (2006.01) |
| H04L 9/32 | (2006.01) |
| H04L 9/08 | (2006.01) |
| G06Q 20/06 | (2012.01) |
| G06Q 20/12 | (2012.01) |
| G16H 10/60 | (2018.01) |

(52) U.S. Cl.
CPC ....... *H04L 9/0637* (2013.01); *G06Q 20/0655* (2013.01); *G06Q 20/127* (2013.01); *G06Q 20/1235* (2013.01); *H04L 9/088* (2013.01); *H04L 9/3239* (2013.01); *H04L 9/3242* (2013.01); *H04L 9/3263* (2013.01); *H04L 9/3265* (2013.01); *H04L 9/3268* (2013.01); *G06Q 20/06* (2013.01); *G16H 10/60* (2018.01); *H04L 2209/38* (2013.01); *H04L 2209/88* (2013.01)

(58) Field of Classification Search
CPC ... H04L 9/0637; H04L 9/3239; H04L 9/3263; H04L 9/088; H04L 9/3265; H04L 9/3242; H04L 9/3268; H04L 2209/38; H04L 2209/88; G06Q 20/127; G06Q 20/1235; G06Q 20/0655; G06Q 20/06; G16H 10/60
USPC ........................................................ 713/157
See application file for complete search history.

(56) References Cited

U.S. PATENT DOCUMENTS

| 8,824,664 | B1 * | 9/2014 | Ristock ................... H04L 63/08 |
| | | | 379/266.03 |
| 9,338,148 | B2 | 5/2016 | Polehn et al. |
| 9,679,276 | B1 * | 6/2017 | Cuende ................ G06Q 20/065 |
| 10,102,526 | B1 * | 10/2018 | Madisetti .............. H04L 9/3239 |

(Continued)

FOREIGN PATENT DOCUMENTS

| KR | 101628005 B1 | 6/2016 |
| WO | 2016032567 A1 | 3/2016 |

OTHER PUBLICATIONS

Anonymously; "System and method for resale of digital assets"; http://ip.com/IPCOM/000206691D; May 2, 2011.

(Continued)

*Primary Examiner* — Aravind K Moorthy

(57) ABSTRACT

An example operation may include one or more of identifying an expiration date associated with an asset, creating a blockchain transaction identifying the asset and the expiration date, storing the blockchain transaction on a blockchain, identifying a requesting entity with a certificate permitting access to the asset, and providing the requesting entity with access to the asset provided the expiration date is still pending.

12 Claims, 9 Drawing Sheets

(56) References Cited

U.S. PATENT DOCUMENTS

| | | | | |
|---|---|---|---|---|
| 10,509,891 | B2* | 12/2019 | Solow | G06F 21/645 |
| 2007/0162762 | A1* | 7/2007 | Huh | H04L 63/06 |
| | | | | 713/182 |
| 2007/0239953 | A1* | 10/2007 | Savagaonkar | G06F 21/78 |
| | | | | 711/163 |
| 2012/0233222 | A1* | 9/2012 | Roesch | H04L 63/1466 |
| | | | | 707/812 |
| 2012/0233458 | A1* | 9/2012 | Sugano | H04L 9/0891 |
| | | | | 713/158 |
| 2013/0132719 | A1* | 5/2013 | Kobayashi | G06F 21/10 |
| | | | | 713/158 |
| 2014/0189808 | A1* | 7/2014 | Mahaffey | H04L 63/083 |
| | | | | 726/4 |
| 2015/0127940 | A1 | 5/2015 | Polehn et al. | |
| 2016/0065571 | A1* | 3/2016 | Hoyos | H04L 63/0435 |
| | | | | 713/168 |
| 2017/0005804 | A1* | 1/2017 | Zinder | H04L 63/123 |
| 2017/0011460 | A1* | 1/2017 | Molinari | G06F 21/645 |
| 2017/0078299 | A1* | 3/2017 | Castinado | H04L 63/102 |
| 2017/0116693 | A1* | 4/2017 | Rae | H04L 9/3236 |
| 2017/0147808 | A1* | 5/2017 | Kravitz | G06F 21/45 |
| 2017/0148016 | A1* | 5/2017 | Davis | G06Q 20/02 |
| 2017/0177640 | A1* | 6/2017 | Gopi | G06F 16/252 |
| 2017/0220815 | A1* | 8/2017 | Ansari | G06F 21/64 |
| 2017/0230189 | A1* | 8/2017 | Toll | H04L 9/3247 |
| 2017/0249482 | A1* | 8/2017 | Takaai | H04L 9/3263 |
| 2017/0250815 | A1* | 8/2017 | Cuende | G06Q 20/401 |
| 2017/0264640 | A1* | 9/2017 | Narayanaswamy | G06F 16/951 |
| 2017/0330180 | A1* | 11/2017 | Song | G06F 21/33 |
| 2017/0346693 | A1* | 11/2017 | Dix | H04L 9/3265 |
| 2017/0352027 | A1* | 12/2017 | Zhang | H04L 9/0825 |
| 2018/0075262 | A1* | 3/2018 | Auh | G06F 21/602 |
| 2018/0115416 | A1* | 4/2018 | Diehl | H04L 9/0838 |
| 2018/0165476 | A1* | 6/2018 | Carey | G06F 21/577 |
| 2018/0167198 | A1* | 6/2018 | Muller | G06F 21/16 |
| 2018/0167200 | A1* | 6/2018 | High | A61B 5/1171 |
| 2018/0183587 | A1* | 6/2018 | Won | H04L 9/0891 |
| 2018/0189312 | A1* | 7/2018 | Alas | G06F 21/64 |
| 2018/0204260 | A1* | 7/2018 | McGregor | G06Q 30/0609 |
| 2018/0225640 | A1* | 8/2018 | Chapman | G06Q 20/10 |
| 2018/0227131 | A1* | 8/2018 | Ebrahimi | H04L 9/3297 |
| 2018/0232121 | A1* | 8/2018 | Lewis | G06F 3/0485 |
| 2018/0262504 | A1* | 9/2018 | Frederick | H04L 63/0435 |
| 2018/0322259 | A1* | 11/2018 | Solow | G06F 21/105 |
| 2018/0323980 | A1* | 11/2018 | Ahn | H04L 9/0631 |
| 2019/0012695 | A1* | 1/2019 | Bishnoi | G06Q 30/0238 |
| 2019/0020468 | A1* | 1/2019 | Rosenoer | H04L 63/0414 |
| 2019/0020471 | A1* | 1/2019 | Santilli | H04L 67/306 |
| 2019/0028514 | A1* | 1/2019 | Barboi | H04L 63/0807 |
| 2019/0114182 | A1* | 4/2019 | Chalakudi | H04L 9/0618 |
| 2019/0123889 | A1* | 4/2019 | Schmidt-Karaca | H04L 9/3239 |
| 2019/0132131 | A1* | 5/2019 | Clements | G06F 21/35 |
| 2019/0179801 | A1* | 6/2019 | Jang | G06F 16/1865 |
| 2019/0199535 | A1* | 6/2019 | Falk | H04L 9/0643 |
| 2019/0230114 | A1* | 7/2019 | Grebovich | H04L 9/0637 |
| 2019/0236562 | A1* | 8/2019 | Padmanabhan | H04L 63/00 |
| 2019/0237169 | A1* | 8/2019 | Culver | H04L 9/3247 |
| 2019/0238525 | A1* | 8/2019 | Padmanabhan | G06F 21/6245 |
| 2019/0251295 | A1* | 8/2019 | Vieyra | G06F 3/0623 |
| 2019/0251573 | A1* | 8/2019 | Toyota | G06Q 10/105 |
| 2019/0268138 | A1* | 8/2019 | Mankovskii | G06F 21/64 |
| 2019/0347444 | A1* | 11/2019 | Lowagie | G06F 21/31 |
| 2020/0076576 | A1* | 3/2020 | Ahlback | H04L 9/0637 |
| 2020/0382306 | A1* | 12/2020 | Wang | G06Q 20/40 |

OTHER PUBLICATIONS

Anonymously; "Universal Blockchained Health Record"; http://ip.com/IPCOM/000245863D; Apr. 13, 2016.

Anonymously; "Usage Verification Probability Based on Asset to Asset Holder Proximity"; http://ip.com/IPCOM/000230729D; Sep. 6, 2013.

Kraft, D.; "Difficulty control for blockchain-based consensus systems"; Peer-to-Peer Networking and Applications, vol. 9, No. 2, pp. 397-413; Mar. 2016.

* cited by examiner

MANAGING ASSETS WITH EXPIRATION ON A BLOCKCHAIN

TECHNICAL FIELD

This application generally relates to managing assets with expiration dates, and more particularly, to managing assets with expiration on a blockchain.

BACKGROUND

A blockchain may be used as a public ledger to store any type of information. Although, primarily used for financial transactions, a blockchain can store any type of information including assets (i.e., products, packages, services, status, etc.). A decentralized scheme transfers authority and trust to a decentralized network and enables its nodes to continuously and sequentially record their transactions on a public "block", creating a unique "chain" referred to as a blockchain. Cryptography, via hash codes, is used to secure an authentication of a transaction source and removes a central intermediary. A blockchain is a distributed database that maintains a continuously-growing list of records in the blockchain blocks, which are secured from tampering and revision due to their immutable properties. Each block contains a timestamp and a link to a previous block. A blockchain can be used to hold, track, transfer and verify any information. Because a blockchain is a distributed system, before adding a transaction to a blockchain ledger, all peers need to reach a consensus status.

Transferring and sharing of digital assets is common in various different domains. For example, in the automotive industry a car or other motorized vehicle may have a digital online title or other identification document that is identified, shared and transferred from owner and/or jurisdiction. In another example, the healthcare industry creates large amounts of patient record data. Such records may require sharing between providers while preserving security. This scenario requires the asset sharing to be secure, immutable, tamper-proof, and distributed for availability among different parties.

SUMMARY

One example embodiment may provide a method that includes one or more of identifying an expiration date associated with an asset, creating a blockchain transaction identifying the asset and the expiration date, storing the blockchain transaction on a blockchain, identifying a requesting entity with a certificate permitting access to the asset, and providing the requesting entity with access to the asset provided the expiration date is still pending.

Another example embodiment may include an apparatus that includes a processor configured to perform one or more of identify an expiration date associated with an asset, create a blockchain transaction which identifies the asset and the expiration date, store the blockchain transaction on a blockchain, identify a requesting entity with a certificate that permits access to the asset, and provide the requesting entity with access to the asset provided the expiration date is still pending.

Yet another example embodiment may provide a non-transitory computer readable storage medium configured to store instructions that when executed cause a processor to perform one or more of identifying an expiration date associated with an asset, creating a blockchain transaction identifying the asset and the expiration date, storing the blockchain transaction on a blockchain, identifying a requesting entity with a certificate permitting access to the asset, and providing the requesting entity with access to the asset provided the expiration date is still pending.

DETAILED DESCRIPTION

Figure 1A:
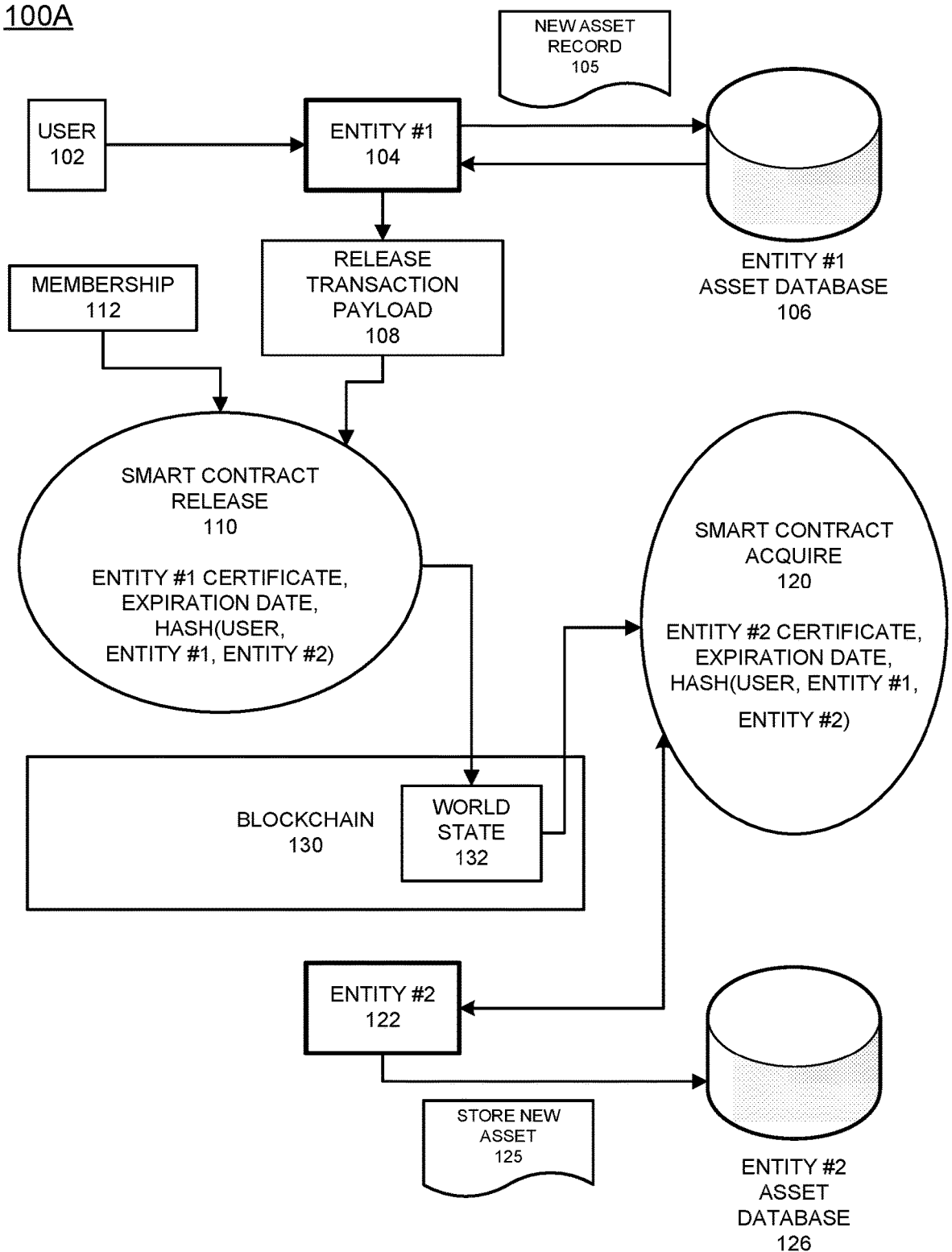
FIG. 1A illustrates a logic network diagram of a limited time asset release and acquisition with a blockchain according to example embodiments.

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed, but is merely representative of selected embodiments.

The instant features, structures, or characteristics as described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" may have been used in the description of embodiments, the application may be applied to many types of network data, such as, packet, frame, datagram, etc. The term "message" also includes packet, frame, datagram, and any equivalents thereof. Furthermore, while certain types of messages and signaling may be depicted in exemplary embodiments they are not limited to a certain type of message, and the application is not limited to a certain type of signaling.

The instant application in one embodiment relates to managing assets with expiration dates, and in another embodiment relates to transferring and managing assets with an access time expiration date on a blockchain.

Example embodiments provide methods, devices, networks and/or systems, which support asset management, such as asset sharing/transfer among different entities. For instance, in the example of an automobile, the asset would be a title which could be digitally defined in a computer accessible file and stored on a server, user computer, agency computer, and shared with privileged parties. The asset may be transferred from one owner to another and/or may be recognized by one jurisdiction and then another at a later time. One approach to managing the digital asset may be an expiration date that expires over the course of a defined period of time that is specified by the asset manager. The expiration period offers the privileged party access to the asset for access purposes, transfer of rights/ownership, etc., for a limited period of time. The expiration would then block out third parties from accessing the asset even if certain credentials, such as a certificate, which was once valid prior to the expiration date, was used by an interested party in an attempt to access the asset. A blockchain may be used to store and secure the asset information. The asset information may be stored in the blockchain or alternatively in a remote temporary database acting as a storage facility that is referenced by the blockchain transaction, which may include various asset information, however, not the entire asset. Off-loading the asset to a storage facility may offer an alternative when the asset size is too large (i.e., large file sizes).

As referred to herein, a blockchain is a distributed system consisting of multiple nodes that communicate with each other. The blockchain runs programs called chaincode (e.g., smart contracts, etc.), holds state and ledger data, and executes transactions. Transactions are operations invoked on the chaincode. Transactions typically must be "endorsed" and only endorsed transactions may be committed and have an effect on the state of the blockchain system. There may exist one or more special chaincodes for management functions and parameters, collectively called system chaincodes.

Nodes are the communication entities of the blockchain system. A "node" is a logical function in the sense that multiple nodes of different types can run on the same physical server. Nodes are grouped in trust domains and associated to logical entities that control them in various ways. Nodes may include different types such as a client or submitting-client node which submits a transaction-invocation to an endorser (e.g., peer), and broadcasts transaction-proposals to an ordering service (e.g., ordering node). Another type of node is a peer node which receives client submitted transactions, commits the transactions and maintains the state and a copy of the ledger. Peers can also have the role of an endorser, although it is not a requirement. The ordering-service-node or orderer is a node running the communication service for all nodes and which implements a delivery guarantee, such as atomic or total order broadcast to each of the peer nodes in the system when committing transactions and modifying the world state.

The ledger is a sequenced, tamper-resistant record of all state transitions of the blockchain. State transitions are a result of chaincode invocations (i.e., transactions) submitted by participating parties (e.g., client nodes, ordering nodes, endorser nodes, peer nodes, etc.) A transaction may result in a set of asset key-value pairs that are committed to the ledger as creates, updates, deletes, and the like. The ledger includes a blockchain (also referred to as a chain) which is used to store an immutable, sequenced record in blocks. The ledger also includes a state database which maintains a current state of the blockchain. There is typically one ledger per channel. Each peer node maintains a copy of the ledger for each channel of which they are a member.

The chain is a transaction log which is structured as hash-linked blocks, and each block contains a sequence of N transactions where N is equal to or greater than one. The block header includes a hash of the block's transactions, as well as a hash of the prior block's header. In this way, all transactions on the ledger may be sequenced and cryptographically linked together. Accordingly, it is not possible to tamper with the ledger data without breaking the hash links. A hash of a most recently added block represents every transaction on the chain that has come before it, making it possible to ensure that all peer nodes are in a consistent and trusted state. The chain may be stored on the peer node file system (either local or attached storage), efficiently supporting the append-only nature of the blockchain workload.

The current state of the immutable ledger represents the latest values for all keys that are included in the chain transaction log. Because the current state represents the latest key values known to the channel, it is sometimes referred to as a world state. Chaincode invocations execute transactions against the current state data of the ledger. To make these chaincode interactions efficient, the latest values of the keys may be stored in the state database. The state database may be simply an indexed view into the chain's transaction log, it can therefore be regenerated from the chain at any time. The state database may automatically get recovered (or generated if needed) upon peer node startup, and before transactions are accepted.

FIG. 1A illustrates a logic network diagram of a limited time asset release and acquisition with a blockchain according to example embodiments. Referring to FIG. 1A, the configuration 100A includes a user device 102 which represents the original owner of the asset being transferred in a sale, purchase, surrender, or other type of negotiation/transaction. The first entity 104 may represent a holder, purchaser, or other entity that is responsible for creating a new asset record, updating a blockchain 130, or more specifically a world state 132 of the blockchain with a smart contract 110 for release of the asset. In operation, the asset is identified by the first entity 104, which may be an institution or other organization, and then the asset record 105 is created in a temporary asset database 106 for record purposes. The information with regard to the asset may be identified in the smart contract and may include a rule that only providers can invoke, an index, which stores the first entity's certificate, the expiration date, the record of the asset (R1), and other information. Also, while storing the assets on the blockchain, one embodiment may use k=hash(User, E1, E2), as the key for the key-value pair on the blockchain, and v=index as the value of that key on the blockchain. The function 'f' may include the identity of the original user, the entities involved, in this example, entity #1 104 and entity #2 122. All this information may be included in the world state of the blockchain, which represents an index or informational foundation of the blockchain in a first blockchain transaction.

A membership 112 provides identity information of one or more parties. The transaction payload 108 represents the asset release information required to access the asset (i.e., permitting the entity #2, 122, to access the asset) in the database 106. Once the release is setup, the acquisition from another entity, such as entity #2 122 may begin. The entity #2 may have its own asset database 126 for storing the asset once acquired. Another smart contract 120 used to acquire the asset may also be created and stored in the world state 132 of the same blockchain 130. The acquire smart contract 120 may provide: k=hash(User, E1, E2), and v=retrievefromWS(k), which is way to read a value of a key 'k' from the blockchain world state. Also, the smart contract 120 may also perform a blockchain verification operation to verify the blockchain is valid and the Merkle hash approach is preserved, a verification operation to verify the entity #1 certificate, verify the certificate expiration date, delete the (k,v) from the world state, and if not expired, return record (R1) to access the asset or provide a null in the event that record cannot be located. The provider entity #2 122 may receive access to the asset and store the asset 125 in the asset database 126. The method of generating the key 'k' and value 'v' are subject to variations in one particular example as hashes could be used to generate keys.

Figure 1B:
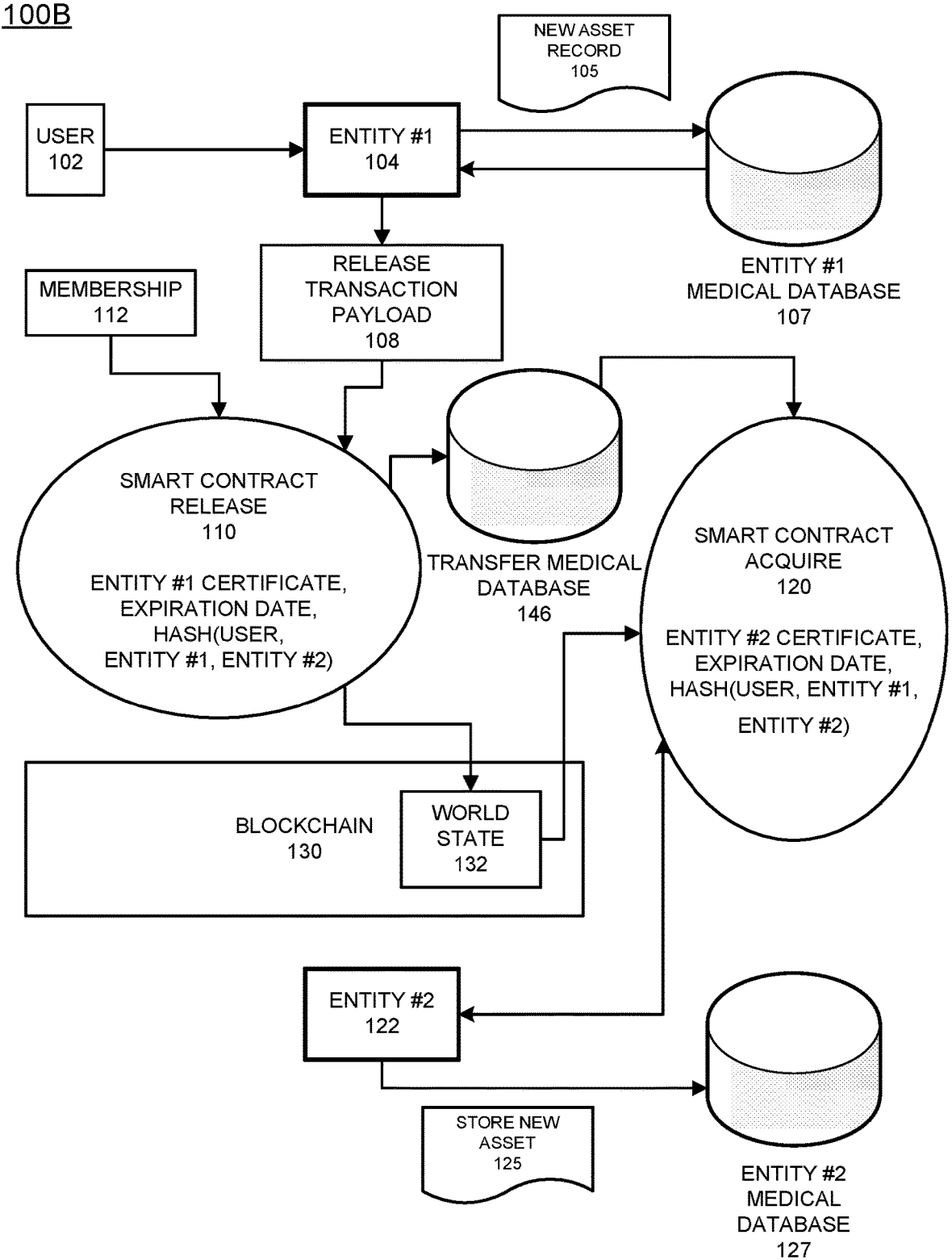
FIG. 1B illustrates a logic network diagram of a limited time asset release and acquisition with a blockchain for a medical record example according to example embodiments.

FIG. 1B illustrates a logic network diagram of a limited time asset release and acquisition with a blockchain for a medical record example according to example embodiments. Referring to FIG. 1B, the configuration 100B includes a user device 102, which represents the original party to the asset being transferred in response to a request, in this example, a medical record is secured and transferred between two entities, such as two institutions. A user, for example, may be a patient who is authorizing entity #2 to access his/her record, by allowing entity #1 to transfer that record (with expiration date) to entity #2 using the Blockchain. The first entity 104 may represent a holder, purchaser, or other entity that is responsible for creating a new asset record 105, updating a blockchain 130, or more specifically a world state 132 of the blockchain with a smart contract 110 for release of the asset. The transfer medical database 146 may also store a copy of entity #1's certificate and the expiration date and other asset/record information. In operation, the asset, or in this example 'record', is identified by the first entity 104, which may be an institution or other organization, and then the asset record 105 is created in a medical asset database 107 for record purposes. The information with regard to the asset may be identified in the smart contract and may include a rule that only providers can invoke, an index, which stores the first entity's certificate, the expiration date, the record of the asset (R1), and other information, such as k=f(User, E1, E2), and v=index. The function 'f' may include the identity of the original user, the entities involved, in this example, entity #1 104 and entity #2 122. All this information may be included in the world state of the blockchain, which represents an index or informational foundation of the blockchain in a first blockchain transaction.

A membership 112 provides identity information of one or more parties. The transaction payload 108 represents the asset release information required to access the asset in the database 107. Once the release is setup, the acquisition from another entity, such as entity #2 122 may begin. The entity #2 may have its own asset database 126 for storing the asset once acquired. Another smart contract 120 used to acquire the asset may also be created and stored in the world state 132 of the same blockchain 130. The acquire smart contract 120 may provide a k=hash(User, E1, E2), v=retrievefromWS (k), a blockchain verification operation to verify the blockchain is valid and the Merkle hash approach is preserved, a verification operation to verify the entity #1 certificate, verify the certificate expiration date, delete the (k,v) from the world state, and if not expired, return record (R1) to access the asset or provide a null in the event that record cannot be located. The provider entity #2 122 may receive access to the asset and store the asset 125 in the medical asset database 127, the transfer may come from the transfer medical database 146 to the entity #2 medical asset database 127. Both the entity databases may be temporary databases where the asset is stored. Over time, the database 146 may fill-up with asset information, a clean-up operation may be used periodically to delete the old assets which are expired. The blockchain may not include the asset itself, but instead certain asset information, which can be used to reference, access and identify the asset. In this medical record example, the record may be a patient test, record, or other medical related documentation.

Figure 2A:
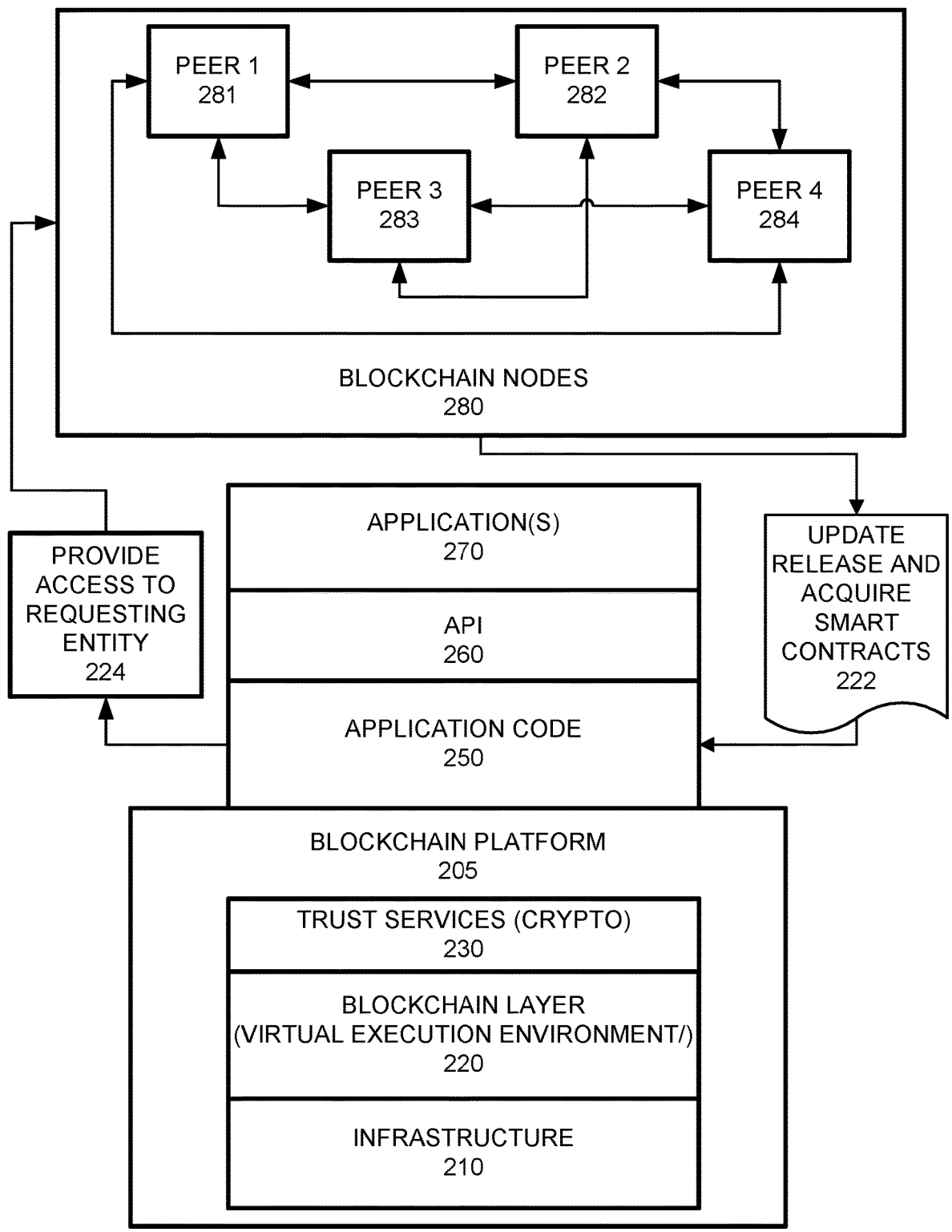
FIG. 2A illustrates an example peer node blockchain architecture configuration for a limited time asset sharing scenario, according to example embodiments.

FIG. 2A illustrates a blockchain system architecture configuration 200A, according to example embodiments. Referring to FIG. 2A, blockchain architecture 200A may include certain blockchain elements, for example, a group 280 of blockchain nodes 281-284 which participate in blockchain transaction addition and validation process (consensus). One or more of the blockchain nodes 281-284 may endorse transactions and one or more blockchain nodes 281-281 may provide an ordering service for all blockchain nodes in the architecture 200A. A blockchain node may initiate a blockchain authentication and seek to write to a blockchain immutable ledger stored in blockchain layer 220, a copy of which may also be stored on the underpinning physical infrastructure 210. The blockchain configuration may include one or applications 270 which are linked to application programming interfaces (APIs) 260 to access and execute stored program/application code 250 (e.g., chaincode, smart contracts, etc.) which can be created according to a customized configuration sought by participants and can maintain their own state, control their own assets, and receive external information. This can be deployed as a transaction and installed, via appending to the distributed ledger, on all blockchain nodes 281-284.

The blockchain base or platform 205 may include various layers of blockchain data, services (e.g., cryptographic trust services, virtual execution environment, etc.), and underpinning physical computer infrastructure that may be used to receive and store new transactions and provide access to auditors which are seeking to access data entries. The blockchain layer 220 may expose an interface that provides access to the virtual execution environment necessary to process the program code and engage the physical infrastructure 210. Cryptographic trust services 230 may be used to verify transactions such as asset exchange transactions and keep information private.

The blockchain architecture configuration of FIG. 2A may process and execute program/application code 250 via one or more interfaces exposed, and services provided, by blockchain platform 205. The code 250 may control blockchain assets. For example, the code 250 can store and transfer data, and may be executed by nodes 281-284 in the form of a smart contract and associated chaincode with conditions or other code elements subject to its execution. As a non-limiting example, smart contracts may be created to execute reminders, updates, and/or other notifications subject to the changes, updates, etc. The smart contracts can themselves be used to identify rules associated with authorization and access requirements and usage of the ledger. For example, hashed identifier information 252 received from a client device may be processed by one or more processing entities (e.g., virtual machines) included in the blockchain layer 220. The result may include access being granted 254 to a third party application from the blockchain computing environment. In this example, the previously known user identifiers or data template information may be stored in the blockchain platform 205. The physical machines 210 may be accessed to retrieve the user device template and the information can be used to match against incoming user identifiers for verification purposes.

Within chaincode, a smart contract may be created via a high-level application and programming language, and then written to a block in the blockchain. The smart contract may include executable code which is registered, stored, and/or replicated with a blockchain (e.g., distributed network of blockchain peers). A transaction is an execution of the smart contract code which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A chaincode may include the code interpretation of a smart contract, with additional features. As described herein, the chaincode may be program code deployed on a computing network, where it is executed and validated by chain validators together during a consensus process. The chaincode receives a hash and retrieves from the blockchain a hash associated with the data template created by use of a previously stored feature extractor. If the hashes of the hash identifier and the hash created from the stored identifier template data match, then the chaincode sends an authorization key to the requested service. The chaincode may write to the blockchain data associated with the cryptographic details. In this example of FIG. 2A, the release and acquire smart contract information may be updated 222 according to the specifications of the entities providing asset services. One function may be to provide the requesting entity, in this example entity #2 with access 224 to the asset if the entity #2 has the correct credentials and the expiration date has not yet matured and is still in an active or pending status (i.e., before the expiration date). The correct credentials are required and the smart contracts conditions must be satisfied prior to releasing the asset access information.

Figure 2B:
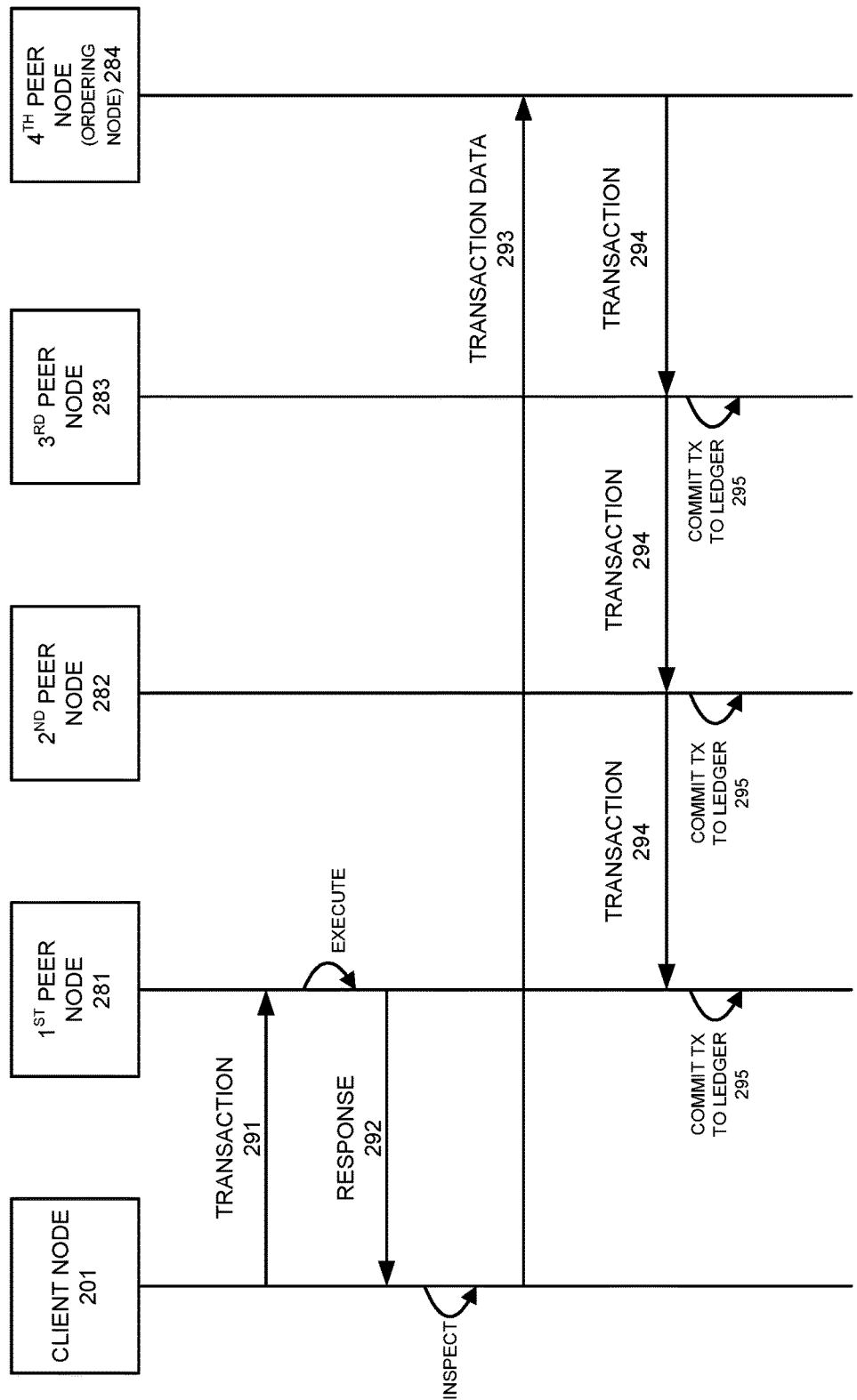
FIG. 2B illustrates an example peer node blockchain configuration, according to example embodiments.

FIG. 2B illustrates an example of a transactional flow 200B between nodes of the blockchain in accordance with an example embodiment. Referring to FIG. 2B, the transaction flow may include a transaction proposal sent by an application client node 201 to an endorsing peer node 281. The endorsing peer 281 may verify the client signature, and execute a chaincode function to simulate the transaction. The output is the chaincode results, a set of key/value versions that were read in the chaincode (read set), and the set of keys/values that were written in chaincode (write set). The proposal response gets sent back to the client 201 along with an endorsement signature. The client assembles the endorsements into a transaction payload and broadcasts it to an ordering service node 284. The ordering service node 284 then delivers ordered transactions as blocks to all peers 281-283 on a channel. Before committal, each peer 281-283 may validate the transactions. For example, they may check the endorsement policy to ensure that the correct allotment of the specified peers have signed the results, and authenticate the signatures against the transaction payload.

Referring to FIG. 2B, in step 291 the client node 201 initiates the transaction by constructing and sending a request to the peer node 281 which is an endorser. The client 201 may include an application leveraging a supported software development kit (SDK) such as Node, Java, Python, and the like, which utilizes an available API to generate a transaction proposal. The proposal is a request to invoke a chaincode function so that data can be read and/or written to the ledger (i.e., write new key value pairs for the assets). The SDK may serve as a shim to package the transaction proposal into a properly architected format (e.g., protocol buffer over gRPC) and take the client's cryptographic credentials to produce a unique signature for this transaction proposal.

In response, the endorsing peer node 281 may verify (a) that the transaction proposal is well formed, (b) the transaction has not been submitted already in the past (replay-attack protection), (c) the signature is valid, and (d) that the submitter (client 201, in the example) is properly authorized to perform the proposed operation on that channel. The endorsing peer node 281 may take the transaction proposal inputs as arguments to the invoked chaincode function. The chaincode is then executed against a current state database to produce transaction results including a response value, read set, and write set. However, no updates are made to the ledger at this point. In step 292, the set of these values, along with the endorsing peer node's 281 signature is passed back as a proposal response to the SDK of the client 201 which parses the payload for the application to consume.

In response, the application of the client 201 inspects/verifies the endorsing peers signatures and compares the proposal responses to determine if the proposal response is the same. If the chaincode only queried the ledger, the application would inspect the query response and would typically not submit the transaction to the ordering service 284. If the client application intends to submit the transaction to ordering service 284 to update the ledger, the application determines if the specified endorsement policy has been fulfilled before submitting (i.e., did peer nodes necessary for the transaction both endorse). Here, the client may include only one of multiple parties to the transaction. In this case, each client may have their own endorsing node, and each endorsing node will need to endorse the transaction. The architecture is such that even if an application chooses not to inspect responses or otherwise forwards an unendorsed transaction, the endorsement policy will still be enforced by peers and upheld at the commit validation phase.

After successful inspection, in step 293 the client 201 assembles endorsements into a transaction and broadcasts the transaction proposal and response within a transaction message to the ordering node 284. The transaction may contain the read/write sets, the endorsing peers signatures and a channel ID. The ordering node 284 does not need to inspect the entire content of a transaction in order to perform its operation; it may simply receive transactions from all channels in the network, order them chronologically by channel, and create blocks of transactions per channel.

In step 294, the blocks of the transaction are delivered from the ordering node 284 to all peer nodes 281-283 on the channel. The transactions within the block are validated to ensure endorsement policy is fulfilled and to ensure that there have been no changes to ledger state for read set variables since the read set was generated by the transaction execution. Transactions in the block are tagged as being valid or invalid. Furthermore, in step 295 each peer node 281-283 appends the block to the channel's chain, and for each valid transaction the write sets are committed to current state database. An event is emitted, to notify the client application that the transaction (invocation) has been immutably appended to the chain, as well as notification of whether the transaction was validated or invalidated.

Figure 3:
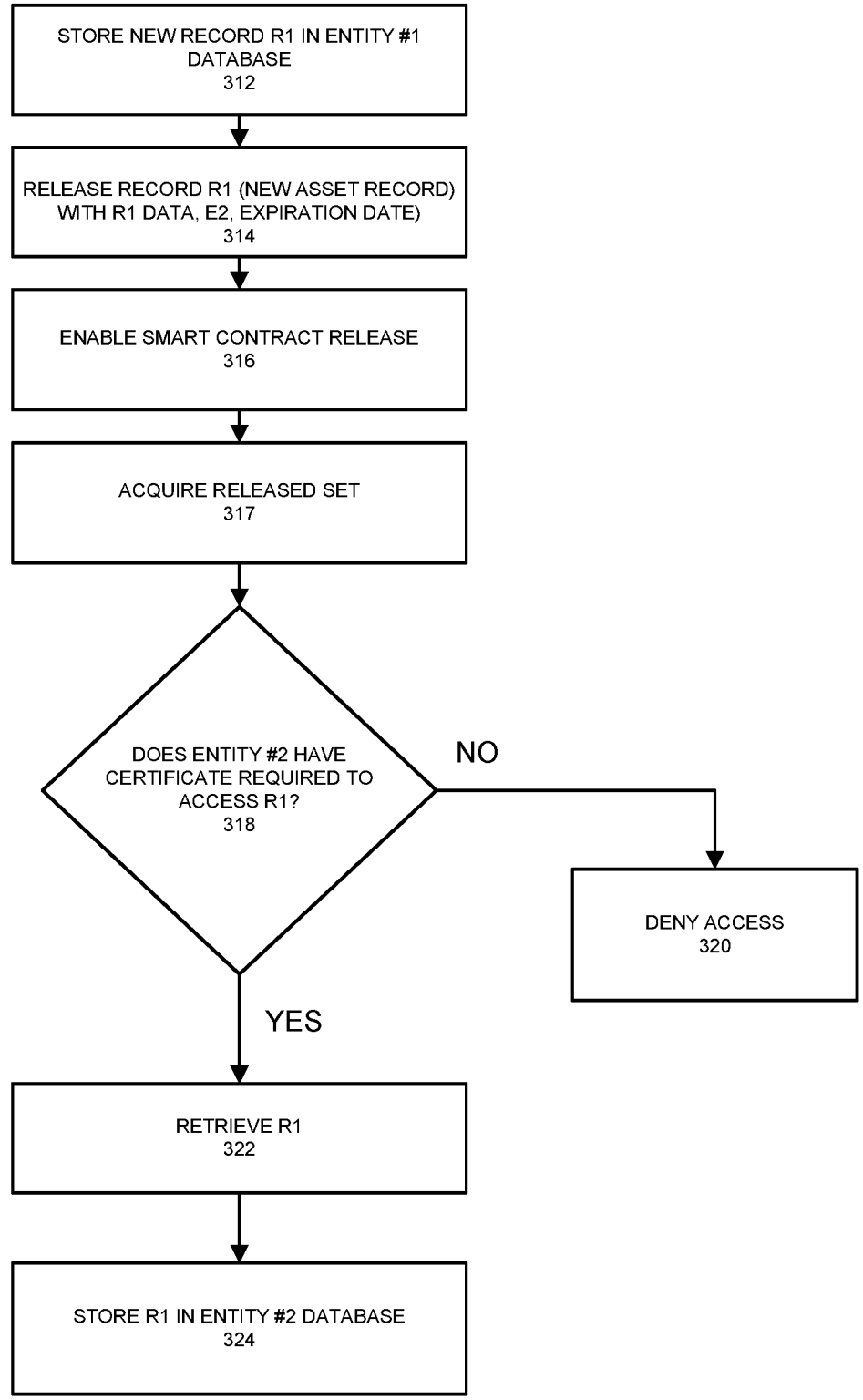
FIG. 3 illustrates a flow diagram of the logic included in an asset record creation with a limited access window, according to example embodiments.

FIG. 3 illustrates a flow diagram of the logic included in an asset record creation with a limited access window, according to example embodiments. Referring to FIG. 3, the method 300 may provide the release of the record R1 as a new asset record. The new record may be stored 312 in the database. The release may include the R1 data, the second entity E2 and the expiration date for the asset sharing 314. The new record R1 may be stored in a database, such as a temporary database used to store the asset information for entity #1. The smart contract for 'release' will help with storing the asset with expiry information in a temporary database. The smart contract 'acquire' may be enabled 316. The released asset is acquired 317, and a determination may be made as to whether entity #2 has the proper credentials (i.e., certificate required to access R1) 318. If not, the process ends 320 with a denied access response. If so, the record R1 may be retrieved 322 and stored in an entity #2 database 324. The blockchain provides access to the record, however, the blockchain may store asset reference information without the actual asset information, which is transferred from private database to private database.

Figure 4:
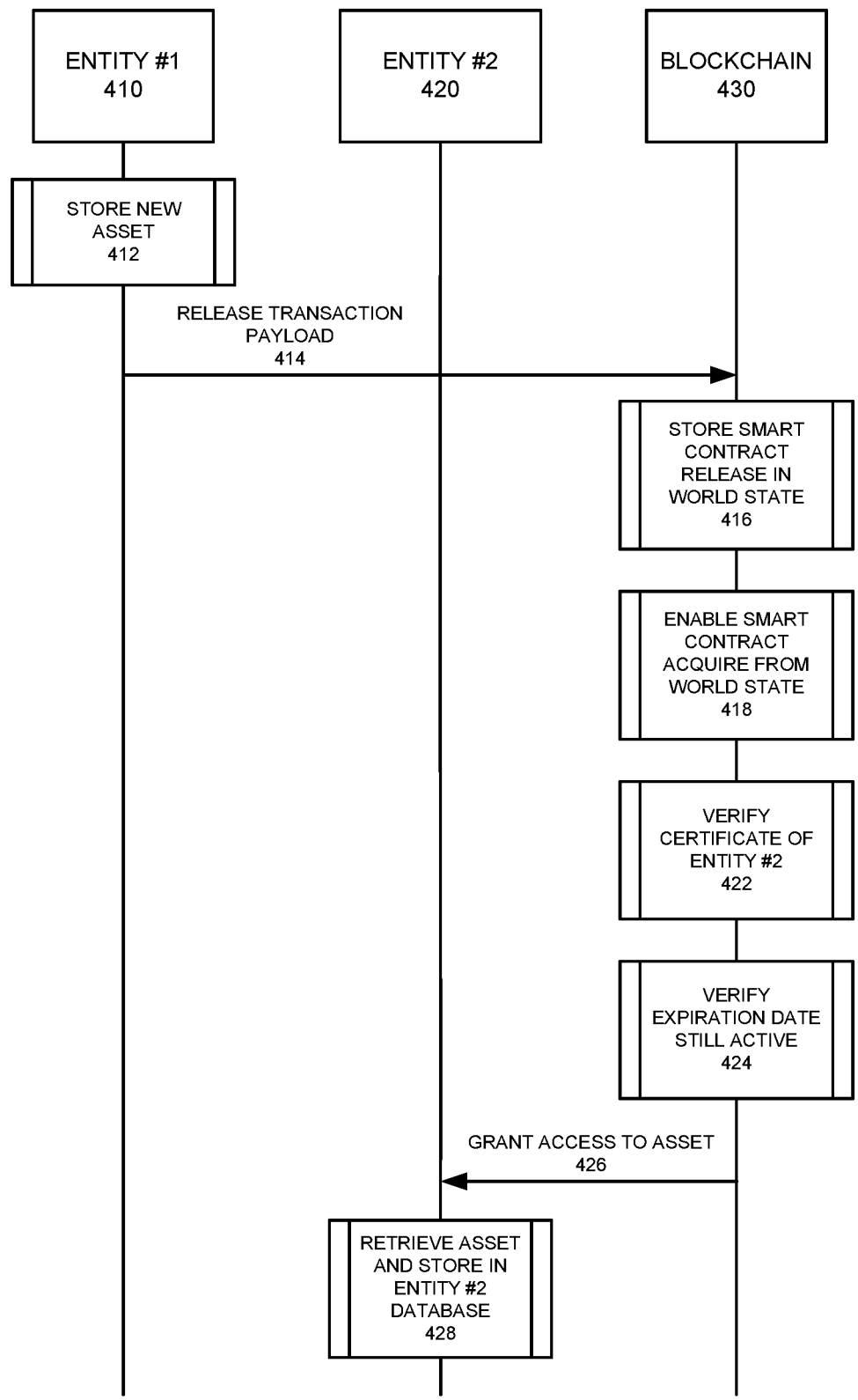
FIG. 4 illustrates a system messaging diagram for performing an asset sharing configuration, according to example embodiments.

FIG. 4 illustrates a system messaging diagram for performing an asset sharing configuration, according to example embodiments. Referring to FIG. 4, the system diagram 400 includes an example where the two entities 410 and 420 are transferring an asset that is identified via the blockchain 430. The example may provide the first entity 410 storing the new asset 412 and releasing a transaction payload 414, which includes the asset information and smart contact information for obtaining access to the asset. The release smart contract may then be formed and stored in a world state 416 of the blockchain 430. The acquire smart contract may also be created and enabled to obtain access to the asset 418. The certification of entity #2 may be verified 422 and the expiration date may be identified as still being active/pending as the expiration deadline may have not been reached/matured 424. The access to the asset may be granted 426 and the asset can then be retrieved and stored in the entity #2 database 428.

Figure 5A:
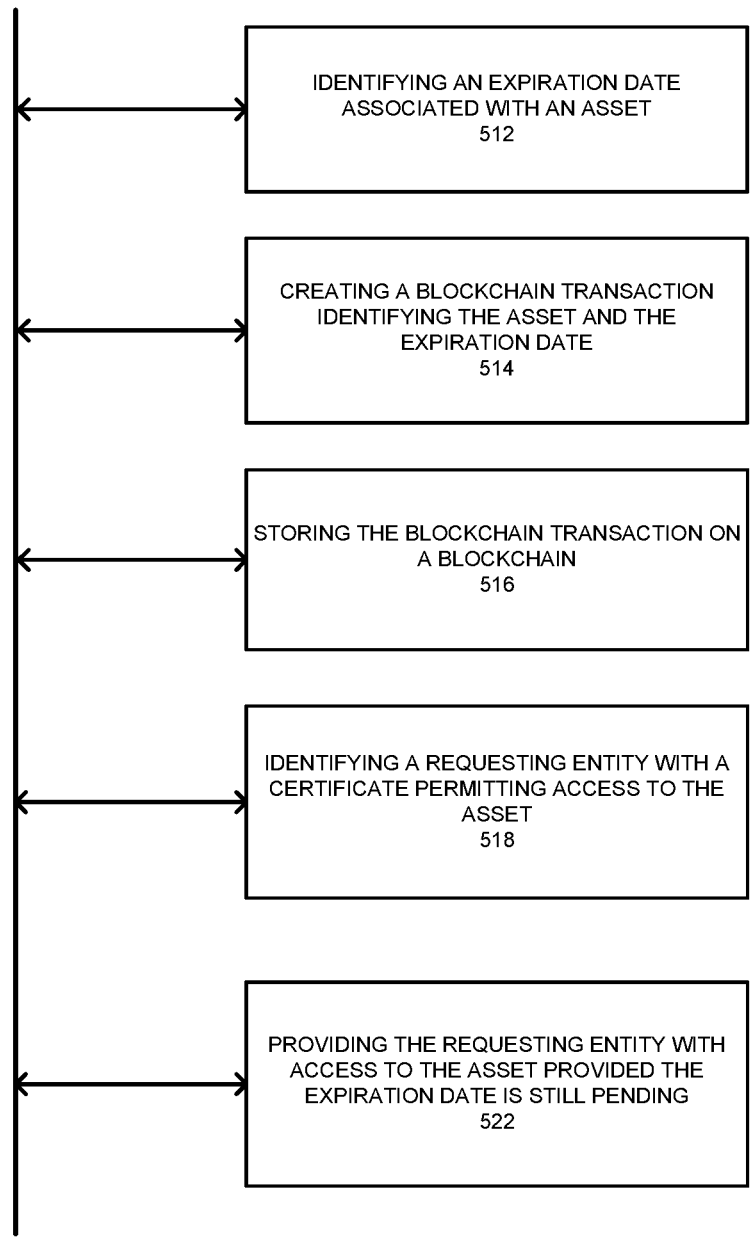
FIG. 5A illustrates a flow diagram of an example method of implementing a time access window for an asset in a blockchain, according to example embodiments.

FIG. 5A illustrates a flow diagram of an example method of implementing a time access window for an asset in a blockchain, according to example embodiments. Referring to FIG. 5A, the method 500 may include identifying an expiration date associated with an asset 512, creating a blockchain transaction identifying the asset and the expiration date 514, storing the blockchain transaction on a blockchain 516, identifying a requesting entity with a certificate permitting access to the asset 518, and providing the requesting entity with access to the asset provided the expiration date is still pending 522. The expiration date may be based on the certificate. The certificate may expire on the expiration date. The method may also include creating a smart contract comprising asset release requirements necessary to access the asset in the blockchain transaction, and the asset release requirements may include the certificate and an access attempt be received prior to expiration of the expiration date. The method may include storing the asset in a temporary database outside the blockchain. The blockchain transaction may include hash information associated with the asset. The method may also include identifying a request to access the asset from the requesting entity, verifying the requesting entity has the credential required to access the asset, and retrieving the asset from the temporary database.

Figure 5B:
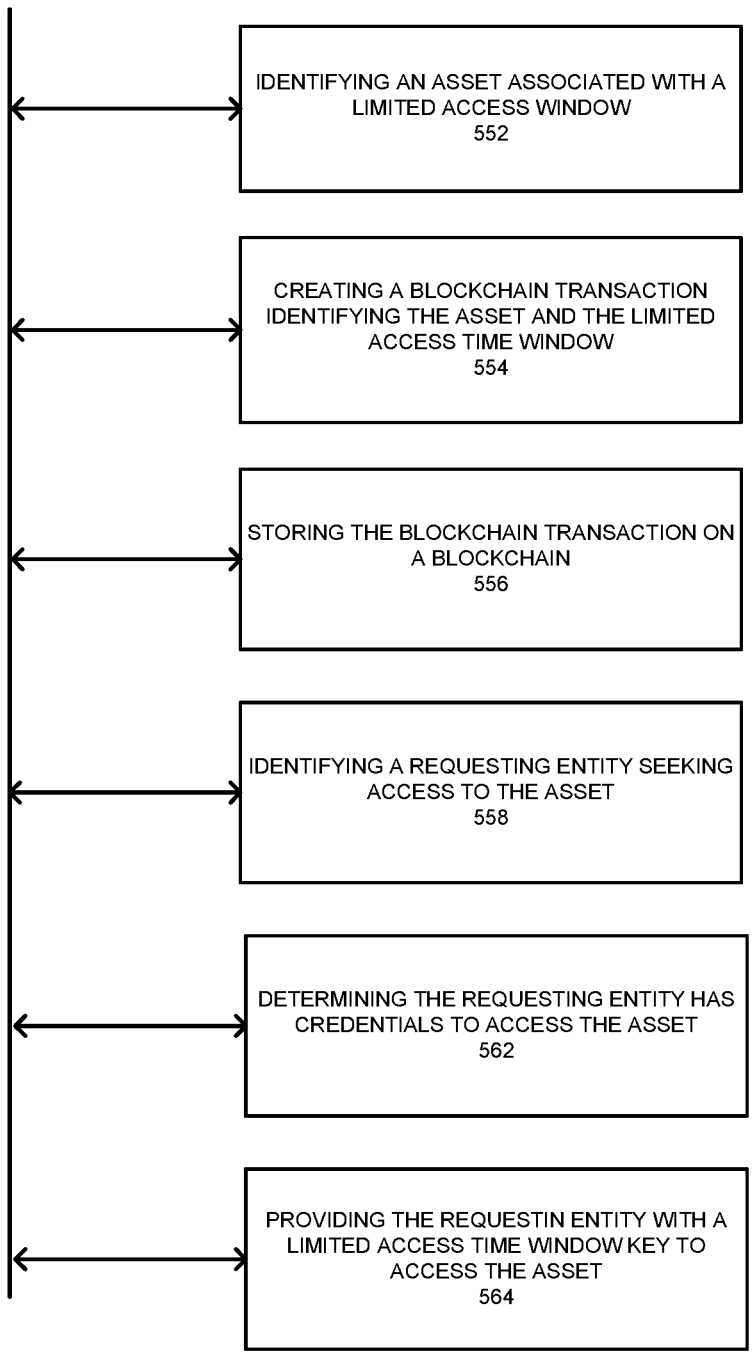
FIG. 5B illustrates a flow diagram of an example method of implementing a time access window for an asset in a blockchain, according to example embodiments.

FIG. 5B illustrates a flow diagram 550 of an example method of implementing a time access window for an asset in a blockchain, according to example embodiments. The method may also include identifying an asset associated with a limited access time window 552, creating a blockchain transaction identifying the asset and the limited access time window 554, storing the blockchain transaction on a blockchain 556, identifying a requesting entity seeking access to the asset 558, determining the requesting entity has credentials to access the asset 562, and providing the requesting entity with a limited access time window key to access the asset 564. In addition to the asset itself being marked or linked to an expiration date, the key provided to decrypt the data to access to the asset may be a limited access key with a limited access time window of opportunity to access the asset data. The key may be replaced with a new key each day, week, etc. and the old key would no longer be valid. The keys can be generated and shared with authorized entities which have the correct credentials necessary to access the asset. However, over the course of limited access window the key may expire and become invalid. Also, public keys (PUB) belonging to the entities and/or the user device may enable the data to be encrypted.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 6 illustrates an example computer system architecture 600, which may represent or be integrated in any of the above-described components, etc.

Figure 6:
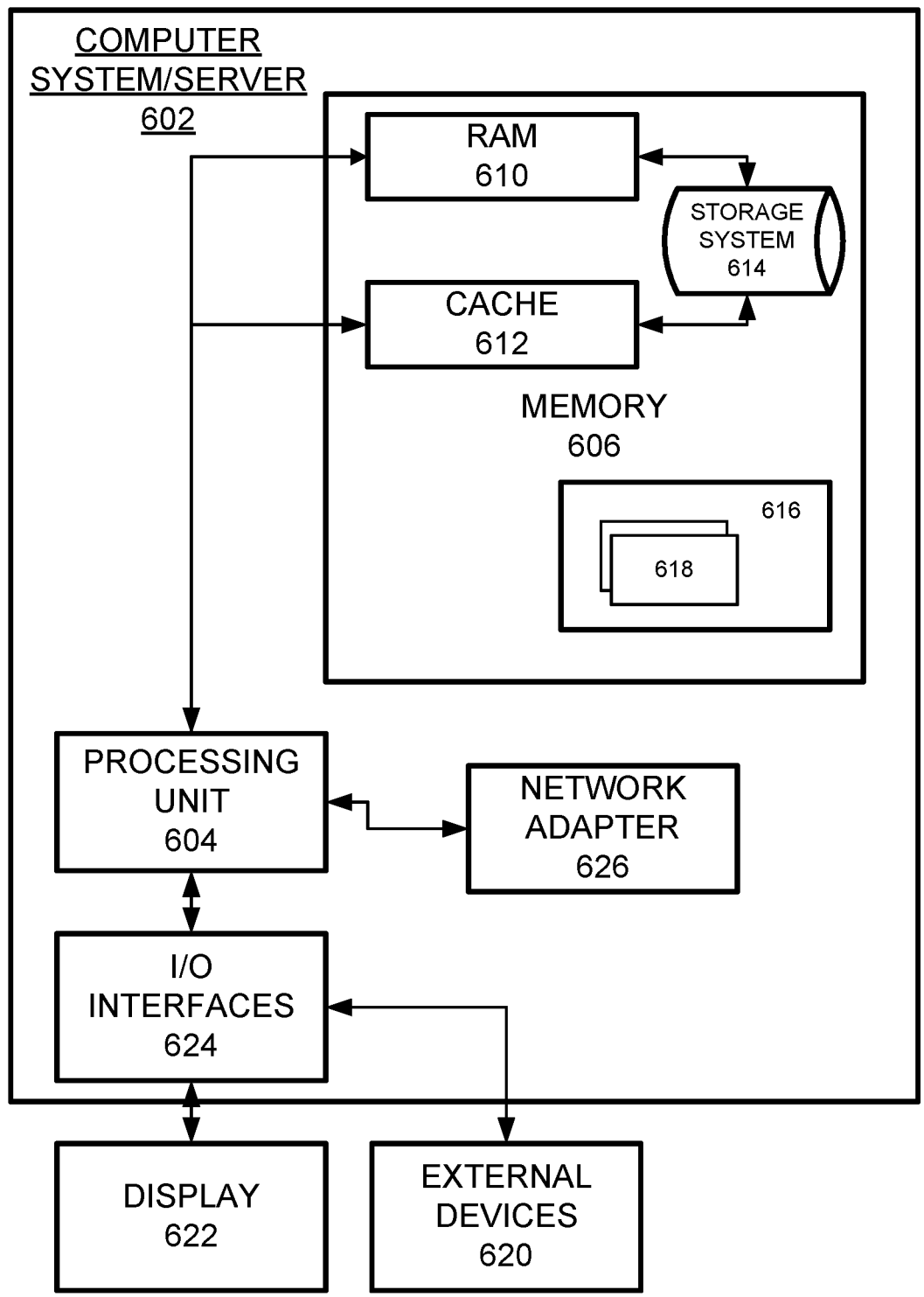
FIG. 6 illustrates an example computer system/server configured to support one or more of the example embodiments.

FIG. 6 is not intended to suggest any limitation as to the scope of use or functionality of embodiments of the application described herein. Regardless, the computing node 600 is capable of being implemented and/or performing any of the functionality set forth hereinabove.

In computing node 600 there is a computer system/server 602, which is operational with numerous other general purpose or special purpose computing system environments or configurations. Examples of well-known computing systems, environments, and/or configurations that may be suitable for use with computer system/server 602 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 602 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 602 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 602 in cloud computing node 600 is shown in the form of a general-purpose computing device. The components of computer system/server 602 may include, but are not limited to, one or more processors or processing units 604, a system memory 606, and a bus that couples various system components including system memory 606 to processor 604.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 602 typically includes a variety of computer system readable media. Such media may be any available media that is accessible by computer system/server 602, and it includes both volatile and non-volatile media, removable and non-removable media. System memory 606, in one embodiment, implements the flow diagrams of the other figures. The system memory 606 can include computer system readable media in the form of volatile memory, such as random access memory (RAM) 610 and/or cache memory 612. Computer system/server 602 may further include other removable/non-removable, volatile/non-volatile computer system storage media. By way of example only, storage system 614 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 606 may include at least one program product having a set (e.g., at least one) of program modules that are configured to carry out the functions of various embodiments of the application.

Program/utility 616, having a set (at least one) of program modules 618, may be stored in memory 606 by way of example, and not limitation, as well as an operating system, one or more application programs, other program modules, and program data. Each of the operating system, one or more application programs, other program modules, and program data or some combination thereof, may include an implementation of a networking environment. Program modules 618 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 602 may also communicate with one or more external devices 620 such as a keyboard, a pointing device, a display 622, etc.; one or more devices that enable a user to interact with computer system/server 602; and/or any devices (e.g., network card, modem, etc.) that enable computer system/server 602 to communicate with one or more other computing devices. Such communication can occur via I/O interfaces 624. Still yet, computer system/server 602 can communicate with one or more networks such as a local area network (LAN), a general wide area network (WAN), and/or a public network (e.g., the Internet) via network adapter 626. As depicted, network adapter 626 communicates with the other components of computer system/server 602 via a bus. It should be understood that although not shown, other hardware and/or software components could be used in conjunction with computer system/server 602. Examples, include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method, comprising:
    receiving, via a first entity, an asset owned by a user;
    generating a hash value based on a combination of an identity of the user, an identity of the first entity, and an identity of a second entity that is allowed to receive access to the asset of the user from the first entity;
    generating a blockchain transaction which includes the hash value and an expiration date identifying when access by the second entity to the asset of the user via the first entity expires; and
    storing the blockchain transaction on a blockchain.

2. The method of claim 1, wherein the asset comprises a medical record of the user which is being shared by the first entity with the second entity for a limited time.

3. The method of claim 1, further comprising:
    creating a smart contract comprising asset release requirements to access the asset in the blockchain transaction, wherein the asset release requirements comprise a certificate of the first entity.

4. The method of claim 1, further comprising:
    storing the asset in a temporary database outside the blockchain.

5. An apparatus, comprising:
    a processor configured to:
        receive, via a first entity, an asset owned by a user;
        generate a hash value based on a combination of an identity of the user, an identity of the first entity, and an identity of a second entity that is allowed to receive access to the asset of the user from the first entity;
        generate a blockchain transaction which includes the hash value and an expiration date identifying when access by the second entity to the asset of the user via the first entity expires; and
        store the blockchain transaction on a blockchain.

6. The apparatus of claim 5, wherein the asset comprises a medical record of the user which is being shared by the first entity with the second entity for a limited time.

7. The apparatus of claim 5, wherein the processor is further configured to create a smart contract comprising asset release requirements to access the asset in the blockchain transaction, wherein the asset release requirements comprise a certificate of the first entity.

8. The apparatus of claim 5, wherein the processor is further configured to store the asset in a temporary database outside the blockchain.

9. A non-transitory computer readable storage medium configured to store one or more instructions that when executed by a processor cause the processor to perform:
    receiving, via a first entity, an asset owned by a user;
    generating a hash value based on a combination of an identity of the user, an identity of the first entity, and an identity of a second entity that is allowed to receive access to the asset of the user from the first entity;
    generating a blockchain transaction which includes the hash value and an expiration date identifying when access by the second entity to the asset of the user via the first entity expires; and
    storing the blockchain transaction on a blockchain.

10. The non-transitory computer readable storage medium of claim 9, wherein the asset comprises a medical record of the user which is being shared by the first entity with the second entity for a limited time.

11. The non-transitory computer readable storage medium of claim 9, wherein the processor is further configured to perform:

creating a smart contract comprising asset release requirements to access the asset in the blockchain transaction, wherein the asset release requirements comprise a certificate of the first entity.

12. The non-transitory computer readable storage medium of claim 9, wherein the one or more instructions are further configured to cause the processor to perform:

storing the asset in a temporary database outside the blockchain.

\* \* \* \* \*